United States Patent [19]
Weigold et al.

[11] Patent Number: 5,707,595
[45] Date of Patent: *Jan. 13, 1998

[54] METHOD AND APPARATUS FOR USE IN PHOTOCHEMICALLY OXIDIZING GASEOUS VOLATILE OR SEMI-VOLATILE ORGANIC COMPOUNDS

[75] Inventors: Theodore S. Weigold, Boise; Adam J. Regner, III, Meridian; John D. Ferrell, Boise, all of Id.

[73] Assignee: Process Technologies, Inc., Boise, Id.

[*] Notice: The term of this patent shall not extend beyond the expiration date of Pat. No. 5,601,184.

[21] Appl. No.: 755,443

[22] Filed: Nov. 22, 1996

Related U.S. Application Data

[63] Continuation-in-part of Ser. No. 536,778, Sep. 29, 1995, Pat. No. 5,601,184.

[51] Int. Cl.⁶ .................................................. B01J 19/12
[52] U.S. Cl. .................................................. 422/186.3
[58] Field of Search .................................................. 422/186.3

[56] References Cited

U.S. PATENT DOCUMENTS

| | | | |
|---|---|---|---|
| 2,998,308 | 8/1961 | Ruth | 23/284 |
| 3,773,044 | 11/1973 | Wallace | 128/142.6 |
| 3,902,485 | 9/1975 | Wallace | 128/142.6 |
| 3,977,952 | 8/1976 | Knoevenagel et al. | 204/157.1 |
| 4,045,316 | 8/1977 | Legan | 204/158 |
| 4,129,418 | 12/1978 | Davis | 422/98 |
| 4,144,152 | 3/1979 | Kitchens | 204/158 |
| 4,146,887 | 3/1979 | Magnante | 340/632 |
| 4,210,503 | 7/1980 | Confer | 204/158 |
| 4,399,686 | 8/1983 | Kindlund et al. | 73/23 |
| 4,468,376 | 8/1984 | Suggitt | 423/358 |

(List continued on next page.)

FOREIGN PATENT DOCUMENTS

| | | |
|---|---|---|
| 0306301 | 3/1988 | European Pat. Off. |
| 0360941 | 4/1988 | European Pat. Off. |
| 0371628 | 6/1989 | European Pat. Off. |
| 51-14619 | 8/1977 | Japan |
| 2165827 | 4/1986 | United Kingdom |

OTHER PUBLICATIONS

Francisco, J.S. et al., "Dissociation Pathways of Carbonyl Halides", *J. Phys. Chem.*, 1989, pp. 8118–8122.

*Primary Examiner*—Charles T. Jordan
*Assistant Examiner*—Daniel Jenkins
*Attorney, Agent, or Firm*—Wells, St. John, Roberts, Gregory & Matkin P.S.

[57] ABSTRACT

A method of forming a sidewall for a reactor for oxidizing volatile or semi-volatile organic compounds, the sidewall being reactive with gaseous oxidation products produced by the oxidation of the volatile or semi-volatile organic compounds, includes, i) providing a dry mixture of material comprising by weight: from about 23% to 35% cement; from about 30% to 45% added CaO; from about 6% to 20% added $Ca(OH)_2$; and from about 10% to 25% added $CaSO_4$; ii) combining the dry mixture of material with water and forming a slurry therefrom; iii) forming the slurry into a desired reactor sidewall shape; and iv) hardening the shaped slurry into a hardened cement reactor sidewall. An apparatus for photochemically oxidizing gaseous volatile or semi-volatile organic compounds includes a reactor vessel comprising sidewalls having at least one baffle. The baffle comprises at least a portion of the respective reaction chamber sidewalls with the baffle itself comprising the dry porous cementitious and chemically sorbent material. The baffle includes a peripheral frame which receives the cementitious material. The frame has a peripheral and inwardly facing channel member having at least two channel walls. The channel walls include at least one projection extending into the cementitious material. A source of ultraviolet light used to produce the oxidation products are U-shaped tubes. A cooling medium used to cool the baffle comprises tubing mounted to a substantially planar substrate.

29 Claims, 9 Drawing Sheets

U.S. PATENT DOCUMENTS

| | | | |
|---|---|---|---|
| 4,499,054 | 2/1985 | Katsura et al. | 422/98 |
| 4,668,489 | 5/1987 | Alexander et al. | 423/240 |
| 4,674,666 | 6/1987 | Foster et al. | 204/164 |
| 4,694,179 | 9/1987 | Lew et al. | 250/431 |
| 4,780,287 | 10/1988 | Zeff et al. | 422/186.3 |
| 4,786,484 | 11/1988 | Nelson | 423/239 |
| 4,847,594 | 7/1989 | Setter | 340/540 |
| 4,892,712 | 1/1990 | Robertson et al. | 422/186 |
| 4,902,311 | 2/1990 | Dingfors et al. | 55/60 |
| 5,352,359 | 10/1994 | Nagai et al. | 210/192 |
| 5,397,552 | 3/1995 | Weigold et al. | 422/186.3 |
| 5,449,443 | 9/1995 | Jacoby et al. | 204/157.3 |
| 5,516,492 | 5/1996 | Dong et al. | 422/186 |
| 5,601,184 | 2/1997 | Weigold | 204/157.15 |

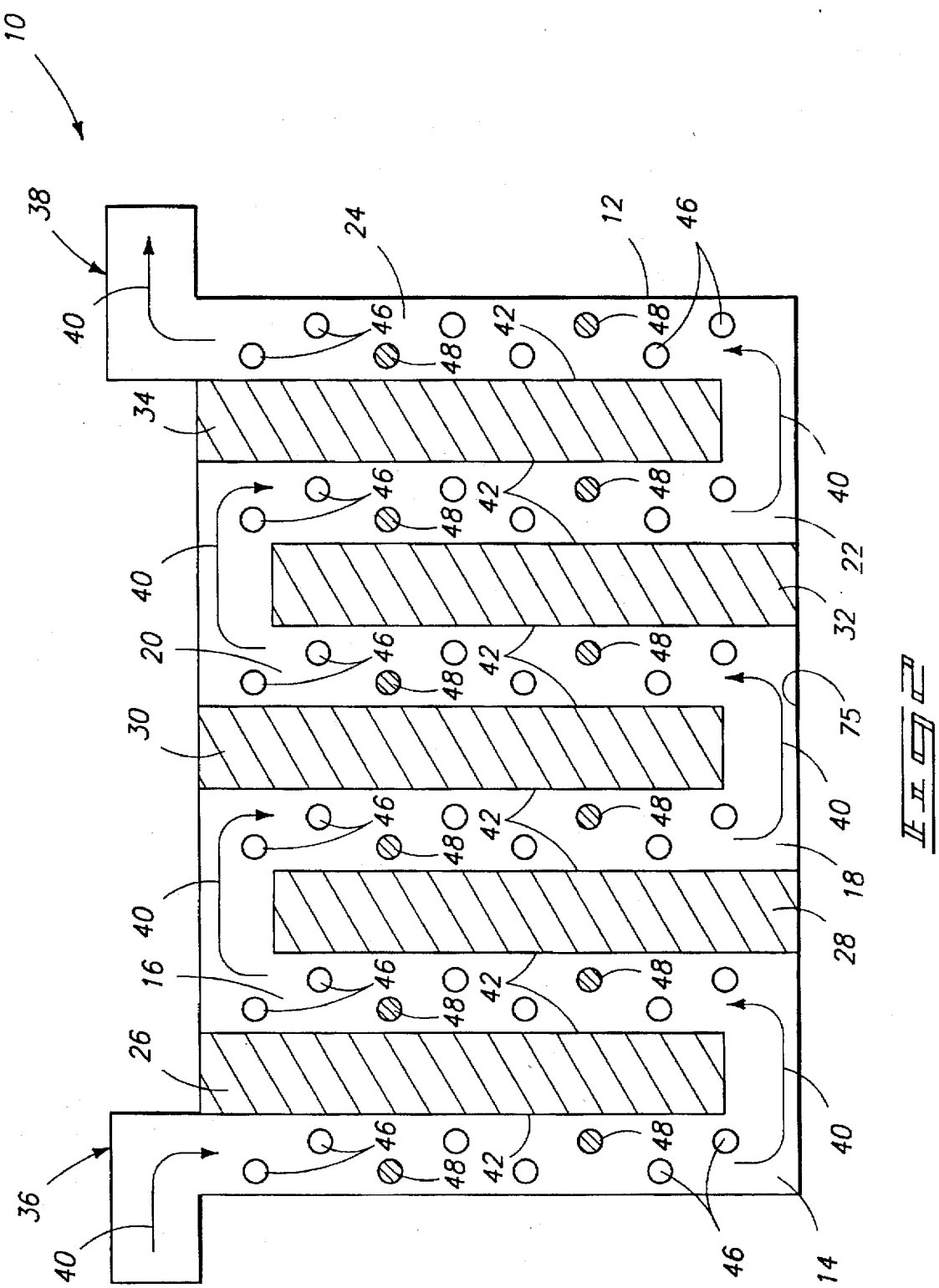

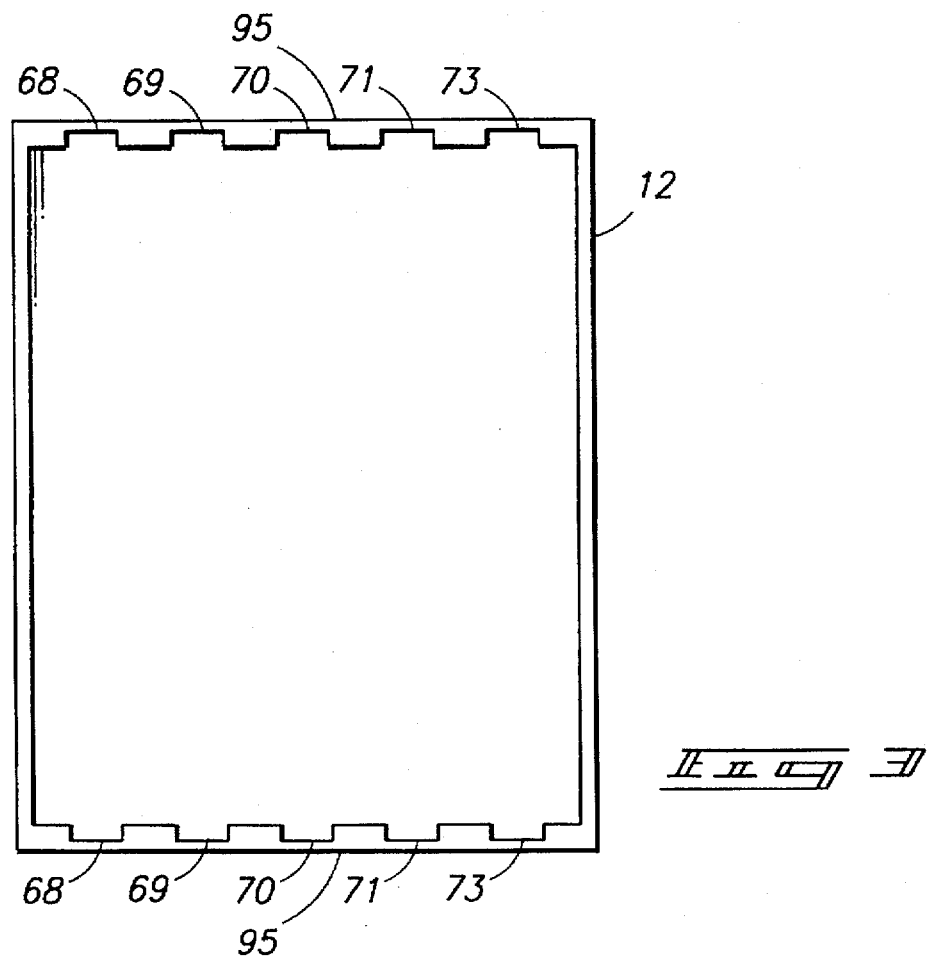
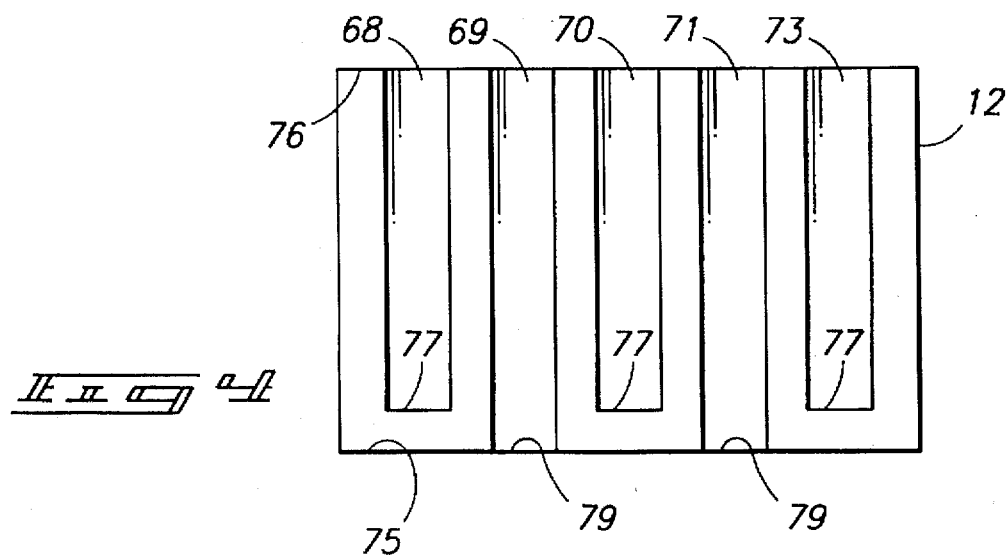

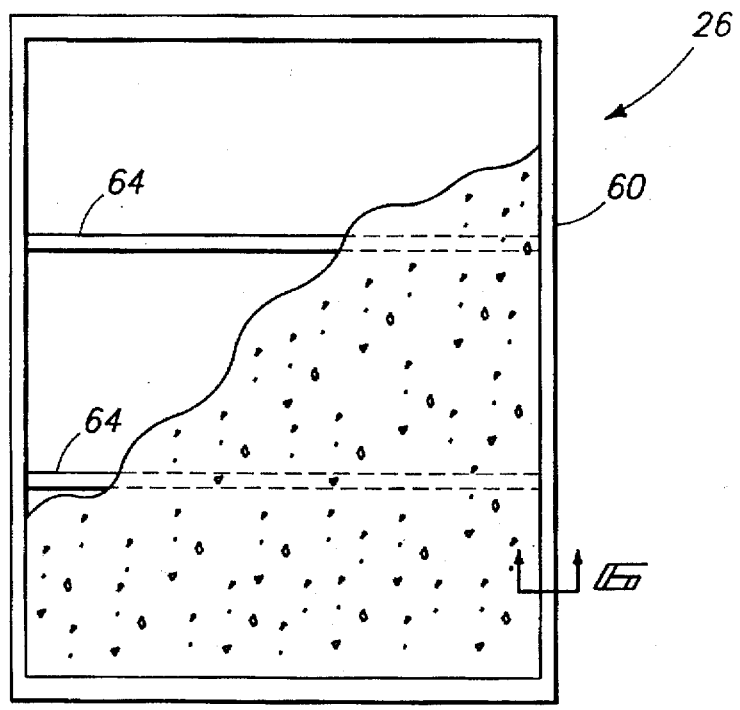
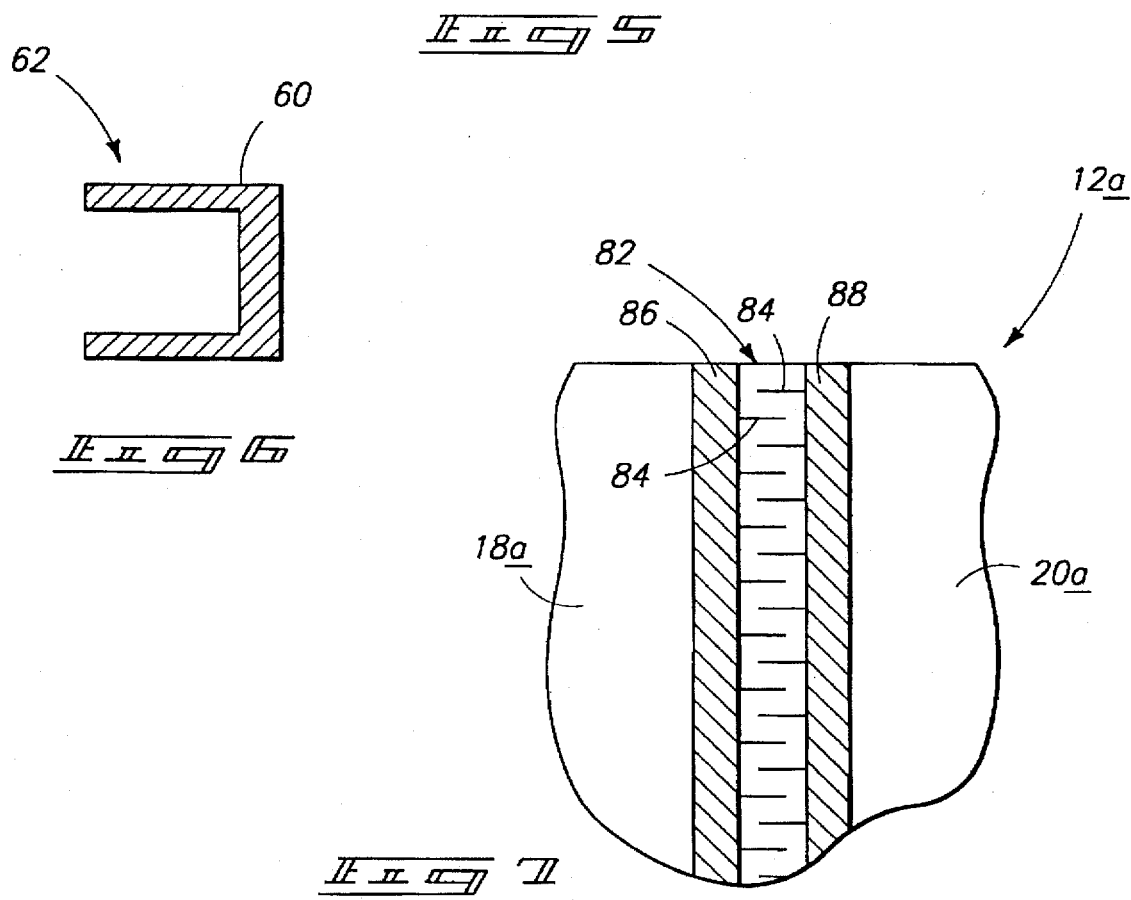

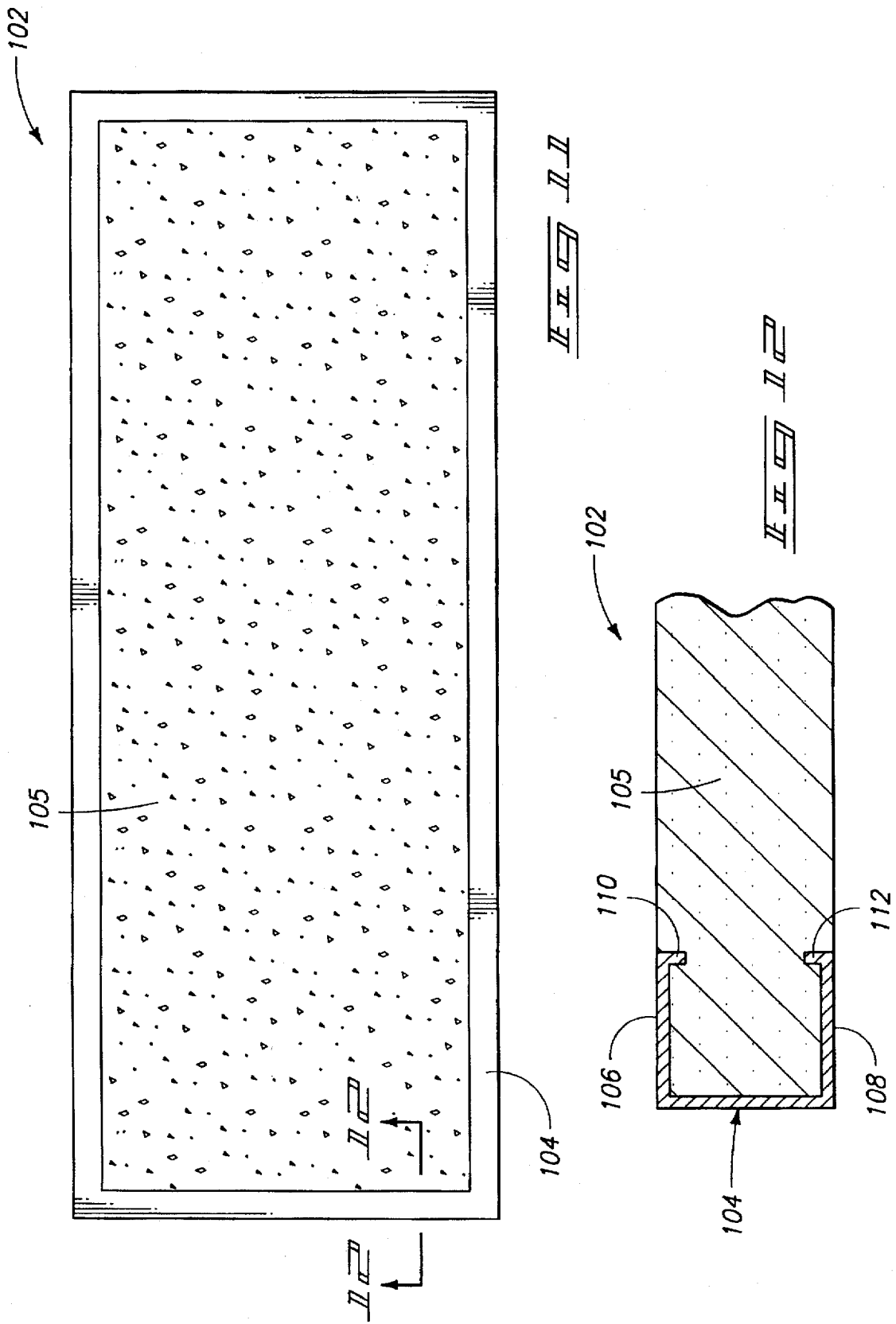

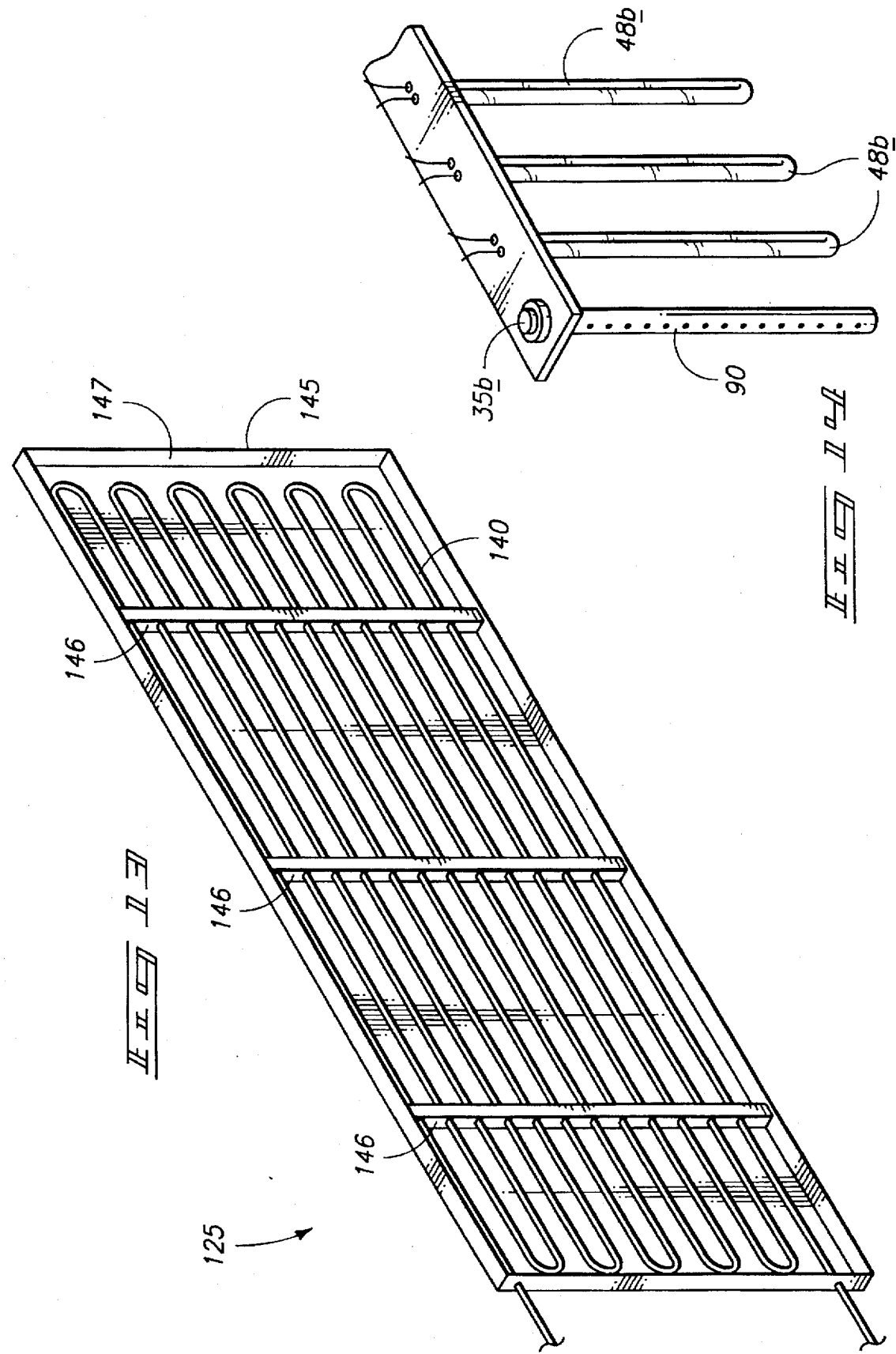

METHOD AND APPARATUS FOR USE IN PHOTOCHEMICALLY OXIDIZING GASEOUS VOLATILE OR SEMI-VOLATILE ORGANIC COMPOUNDS

RELATED PATENT DATA

This patent resulted from a continuation-in-part application of U.S. patent application Ser. No. 08/536,778, filed Sep. 29, 1995, entitled "Method And Apparatus For Use In Photochemically Oxidizing Gaseous Volatile Or Semi-Volatile Organic Compounds", listing Theodore S. Weigold as the inventor, and which is now U.S. Pat. No. 5,601,184.

TECHNICAL FIELD

This invention relates to methods for use in photochemically oxidizing volatile and semi-volatile organic compounds.

BACKGROUND OF THE INVENTION

A fragile and invisible layer of ozone some nine to fifty kilometers above shields the earth's surface against harmful ultraviolet radiation from the sun. It has been discovered that this protective shield is being massively depleted. Such is generally accepted to largely be the result of man-made chemicals that have been and continue to be released into the atmosphere.

Ozone is naturally produced in the stratosphere. Molecular oxygen, $O_2$, is naturally photodisassociated into free oxygen atoms under the influence of radiation from the sun. Such production of oxygen atoms leads immediately to the production of ozone molecules as shown in the following equation, $$O_2 + O + M \rightarrow O_3 + M,$$

where a triple collision between a molecule of oxygen $O_2$, an atom of oxygen O, and a third particle "M", which may be a molecule of oxygen or of nitrogen, which absorbs excess reaction energy and results in formation of a molecule of ozone, $O_3$.

Ozone-depleting chemicals fall into four major groups. The first is known as chlorofluorocarbons (CFC's). These are used as aerosol propellants, refrigerants, blowing agents, solvents and sterilants. Freon-12 (dichlorodifluoromethane) is one example. A second group is known as "halons", which are bromine-containing chemicals used as fire suppressants. A third group is known as chlorocarbons, and include chemicals such as carbon tetrachloride and 1,1,1-trichloromethane. A fourth group consists of relatives of the CFC's called "hydrochlorofluorocarbons" (HCFC's). These are widely used as interim substitutes for some CFC's, and typically have from 2% to 10% of the ozone-destroying power of CFC's.

When released during production and use, it is believed that ozone-depleting chemicals remain in the atmosphere for decades, some even for centuries. Once released, they are atmospherically heated, wind and air current dispersed, and ultimately rise to 10 to 15 kilometers. There, ultraviolet light in the wavelength range of from 170 to 230 nanometers breaks the molecules apart. This releases chlorine, fluorine or bromine which contribute to the destruction of ozone and the formation of ordinary oxygen, a substance which is useless for screening out dangerous ultraviolet radiation from the sun.

Once the molecules are broken, some of the fluorine combines with hydrogen to form HF. Ultimately, the fluorine is precipitated into the lower atmosphere where it ends up in water solution. Carbon freed from the halogenated organic compounds combines with available oxygen to form $CO_2$. Such is chemically benign, but physically contributes to global warming which is commonly referred to as the "greenhouse effect". Also, the gaseous halogenated organic compounds while in the lower atmosphere on their way to the stratosphere are believed to themselves absorb infrared radiation reflected from the earth's surface, thereby converting it into heat and contributing to global warming. Ozone-depleting chemicals are believed responsible for 20% to 25% of current increases in the greenhouse effect.

Combination of carbon with free oxygen to form $CO_2$ is also believed to adversely affect $O_3$ production. The carbon in essence consumes some of the raw material (free oxygen) out of which $O_3$ is naturally made in the atmosphere.

Free chlorine atoms from the ultraviolet light dissociation of the halogenated organic gases would have a tendency to combine with one another to form chlorine gas ($Cl_2$), but for available free oxygen atoms available in the atmosphere. The pollutant chlorine atoms have a greater tendency to join with free oxygen atoms to form a chlorine oxide ($ClO_x$), again consuming one of the principal raw material (free oxygen) out of which $O_3$ is made.

As the ozone layer is depleted, more harmful ultraviolet radiation reaches the earth's surface. Unless ozone depletion is stopped, adverse global health and environmental consequences on a large scale are predicted to occur. The Environmental Protection Agency (EPA) has predicted that increased ultraviolet radiation from ozone depletion would cause between 163,000,000 and 308,000,000 extra cases of skin cancer in the U.S. alone, among people alive today and born by 2075, if nothing were done to save the ozone layer. About 3.5 to 6.5 million of these cases are predicted to be fatal. More ultraviolet radiation would also cause an estimated 19 to 29 million additional cases of cataracts in this population. Sharp increases in the number and variety of serious immunological disorders are also predicted. Further, damage to the natural environment from increased ultraviolet radiation would range from billions of dollars in reduced crop yields to disruption of the marine food chain.

It is not surprising then that research is underway for substitutes for these gaseous halogenated organic compounds. However, it is estimated that it may take 20 years or more to find acceptable substitutes. Consider that the substitute will need to be benign, non-flammable, stable, inexpensive and safe for use in homes (i.e. for refrigeration and aerosol propellants). Accordingly, people are as well working on techniques for preventing these gaseous halogenated organic compounds from entering the atmosphere.

One potentially promising technique for avoiding release of these gases exposes the objectionable materials to ultraviolet radiation for destruction under controlled conditions. Examples of such techniques are disclosed in U.S. Pat. No. 4,210,503 to Confer and U.S. Pat. No. 4,045,316 to Legan. However, a problem associated with any such reactive systems is how one disposes of the reaction byproducts which are produced by the photochemical oxidation. While CFC's and HCFC's are rather inert to humans, the oxidation products produced by such reactors are very harmful to life. Additionally, the oxidation products can be corrosive, explosive or otherwise harmful or destructive to the reactor system and its components. Accordingly, it would be desirable to develop alternate methods and techniques for contending with the hazardous oxidation byproducts produced by such photochemical oxidations.

Hereby incorporated by reference are U.S. Pat. Nos. 5,260,036; 5,374,404; and 5,397,552.

BRIEF DESCRIPTION OF THE DRAWINGS

Preferred embodiments of the invention are described below with reference to the following accompanying drawings.

FIG. 2 is an enlarged diagrammatic end view of the FIG. 1 apparatus.

FIG. 3 is a partial, reduced size, diagrammatic top view of the FIG. 1 apparatus.

FIG. 4 is a reduced diagrammatic view of an end wall of the FIG. 1 apparatus.

FIG. 5 is a diagrammatic, fragmentary top view of a removable baffle lining used in the FIG. 1 apparatus.

FIG. 6 is a sectional view taken along line 6—6 in FIG. 5, with the cementitious material of FIG. 5 not being shown for clarity.

FIG. 7 is a fragmentary diagrammatic top view of an alternate preferred embodiment apparatus for photochemically oxidizing gaseous volatile or semi-volatile organic compounds in accordance with the invention.

FIG. 11 is a side elevational view of a baffle liner used in the apparatus of FIG. 8.

FIG. 12 is a sectional view taken through line 12—12 in FIG. 11.

FIG. 13 is a diagrammatic perspective view of cooling tubing mounted to a substantially planar substrate, which is used in the apparatus of FIG. 8.

FIG. 14 is a fragmentary, diagrammatic perspective view of a portion of a light a gas diffuser mounting plate used in the apparatus of FIG. 8.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

Figure 1:
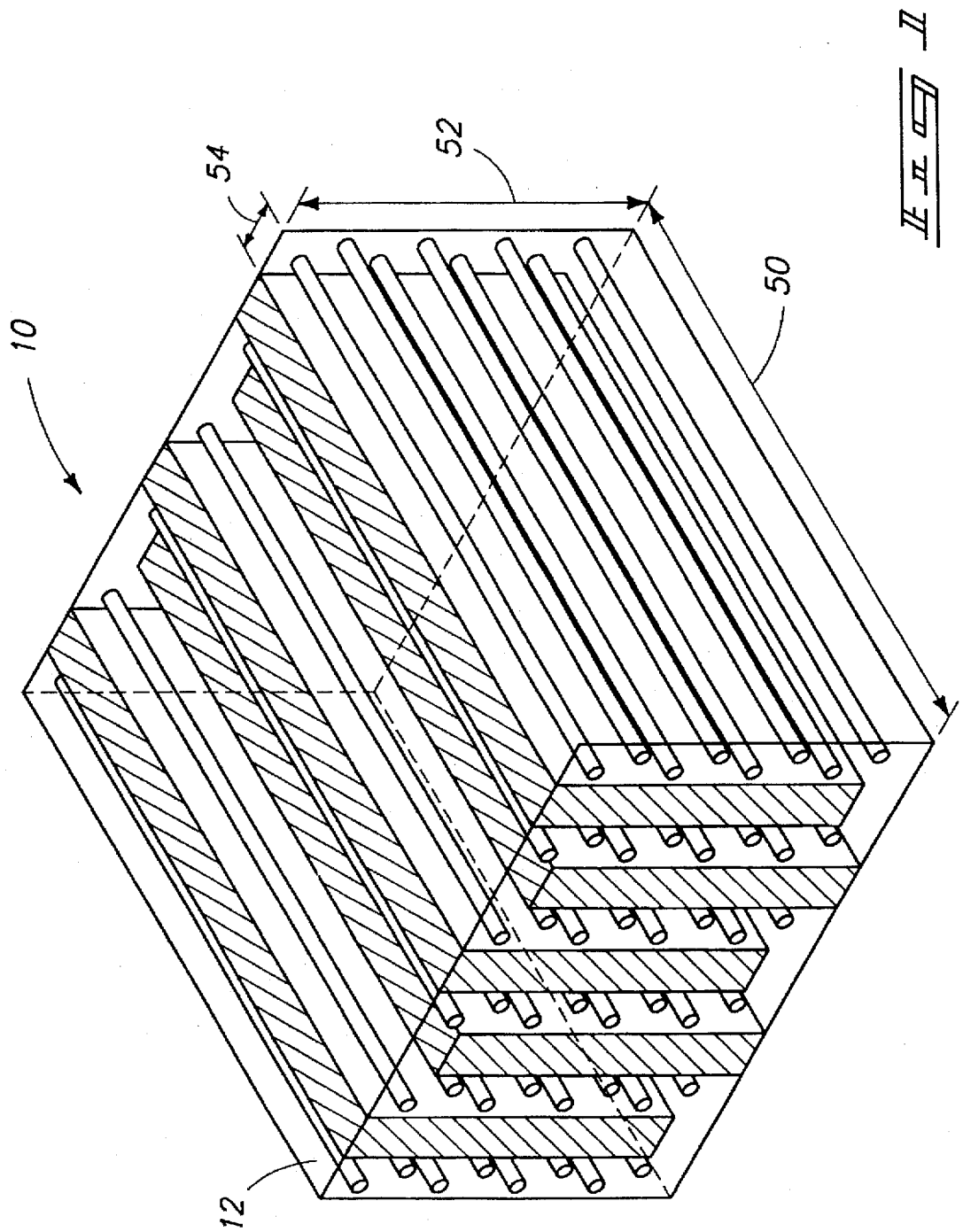
FIG. 1 is a diagrammatic perspective view of a preferred embodiment apparatus for photochemically oxidizing gaseous volatile or semi-volatile organic compounds in accordance with the invention.

Referring to FIGS. 1 and 2, an apparatus for photochemically oxidizing gaseous volatile or semi-volatile organic compounds is indicated generally with reference numeral 10. Such is comprised of a reactor vessel 12 having a plurality of reaction chambers 14, 16, 18, 20, 22 and 24 provided therein. Vessel 12 is preferably composed of aluminum or a graphite fiberglass reinforced composite. A series of baffles 26, 28, 30, 32 and 34 are mounted relative to reactor vessel 12. A gas inlet 36 and a gas outlet 38 are provided relative reactor vessel 12, but are not shown in FIG. 1 for clarity in FIG. 1. Each preferably comprises an elongated plenum having a plurality of laterally spaced orifices (not shown) for providing the desired inlet and outlet of gases. Baffles 26, 28, 30, 32 and 34 define a serpentine gas flow path 40 within reactor vessel 12 between gas inlet 36 and gas outlet 38. Such baffles further define lining sidewalls 42 of the respective reaction chambers 14, 16, 18, 20, 22 and 24. The illustrated reaction chambers are elongated both in a direction 50 perpendicular to gas flow path 40 and in a direction 52 parallel to gas flow path 40 within the respective chambers. Baffles 26, 28, 30, 32 and 34 define the illustrated reaction chambers to have a substantially constant depth along a direction 54. The example construction shows five baffles and six reaction chambers. More or less could of course be utilized.

A source of ultraviolet light is provided within and along the reaction chambers to oxidize gaseous volatile or semi-volatile organic compounds fed to the reaction chambers into gaseous oxidation products. Preferably, the source of ultraviolet light comprises a series of elongated ultraviolet light tubes 46. The apparatus further preferably comprises a series of elongated cooling tubes 48 interspersed among light tubes 46 and which run parallel therewith within reaction chambers 14, 16, 18, 20, 22 and 24. Light tubes 46 and cooling tubes 48 run substantially parallel with the baffles along direction 50 and substantially perpendicular to serpentine gas flow path 40. A preferred operating temperature is 285° F.

Baffles 26, 28, 30, 32 and 40 are constructed such that sidewalls 42 of the respective reaction chambers comprise a dry porous cementitious and chemically sorbent material which is chemically reactive with the gaseous oxidation products produced from the ultraviolet light source to produce solid reaction products which become incorporated in the reaction chamber sidewalls. Example preferred materials, example feed gases, example gaseous oxidation products, and example solid reaction products are described in our U.S. Pat. Nos. 5,260,036; 5,374,404; and 5,397,552.

Most preferably, baffles 26, 28, 30, 32 and 34 are mounted to be slidably removable from reactor vessel 12 without moving or otherwise disturbing light sources 46. A preferred baffle construction and channel design for accommodating such slidable and removable baffling support assembly is described with reference to FIGS. 3–6. Referring first to FIGS. 5 and 6, one example removable reaction chamber baffle liner 26 is shown. Such is comprised of a rectangular peripheral aluminum support frame 60 which is sized and shaped for sliding receipt within photochemical oxidation reactor vessel 12. Such preferably comprises a peripheral and inwardly facing channel member 62 about the frame periphery. A pair of cross-extending support bars 64 provides additional support. Framework 60 comprises a support network for supporting a hardened mass of the dry porous cementitious and chemically sorbent material.

A preferred process for assembling a baffle 26 would be to initially place framework 60 upon a suitable surface such as wood or paper supported on a hard surface. An appropriate cement mix would be mixed and poured into frame 60 such that it completely fills the volume and area internal of peripheral frame 60. Such material would typically expand slightly upon hardening to form a hardened mass which is self supporting in combination with framework 60. One example mix for a given frame size is provided below.

| Baffle Linings: | |
| --- | --- |
| Frame Size | 18.5" × 57.5" × 5/8" |
| Fondue Cement | 1534 g |
| CaO | 605 g |
| Ca(OH)$_2$ (raw) | 355 g |
| Ca(OH)$_2$ (treated) | 712 g |

-continued

| Baffle Linings: | |
|---|---|
| $Al_2O_3$ | 1576 g |
| Al | 39.8 g |
| Water | 5.53 L |
| Fiberglass | 350 g |
| Total grams: | 4821.8 g |

The above listed raw $Ca(OH)_2$ is out-of-the-bag, as-purchased calcium hydroxide. The treated $Ca(OH)_2$ is calcium hydroxide which has been exposed to carbon dioxide. It has been discovered that providing a portion of the calcium hydroxide to the mix which has been treated with $CO_2$ facilitates the time for hardening of the mix into a solidified mass. An example preferred technique for providing such treated calcium hydroxide is to combine a weight ratio of calcium hydroxide to dry ice of 5:1 by weight, and suitably mixing the two solid materials together for an example time period of 120 minutes in a suitable mixing or tumbling apparatus. As listed, the mix also preferably comprises homogeneously interspersed structural reinforcing fiberglass fibers, with individual fibers having an example length of ½ inch.

The discussion proceeds with reference to FIGS. 3 and 4 of an example reactor vessel design which facilitates slidable insertion and removal of the preferred baffles without disturbing the ultraviolet light source. Specifically, opposing end walls 95 of reactor vessel 12 are provided with a plurality of pairs 68, 69, 70, 71 and 73 of opposing internal channels provided within reactor vessel 12. Individual baffles are slidably and removably received within the respective pairs of channels. The illustrated channels are shown as being provided as indentations into end walls 95. Alternate constructions could of course be utilized. For example, channeled members could be provided and secured by bolts or other means relative to the internal surfaces of reaction chamber 12.

Referring to FIG. 4, reactor vessel 12 has an internal floor 75. A first set 68, 70 and 73 of the pairs of opposing channels are provided with baffle support bases 77. These are positioned above internal reactor vessel floor 75 and effectively position a first set of baffles 26, 30 and 34 received by first set of channels 68, 70 and 73 above reactor vessel floor 75. A second set 69 and 71 of the pairs of opposing channels are provided with baffle support bases 79 which effectively coincide with reactor vessel floor 75. Such position a second baffle set 28 and 32 sealingly against reactor vessel floor 75.

In accordance with one aspect of the invention, reactive gases to be treated by the system would be fed to reactor vessel 12 at reactor inlet 36. Such gases would be treated in accordance with the methods disclosed and claimed in U.S. Pat. Nos. 5,260,036; 5,374,404; and 5,397,552.

An alternate example cooling construction with associated baffles is described with reference to FIG. 7. Such illustrates a fragmentary top view of an alternate embodiment reactor vessel 12a. Such illustrates one cooling fluid passageway 82 of a plurality of such passageways which are received within the reactor vessel and run parallel relative to pairs of baffles. Cooling fluid passageway 82 is provided with a series of baffling 84 therethrough to direct cooling flow laterally across the vessel between a pair of baffle lining sidewalls. Cooling fluid passageway 82 is sandwiched between and immediately adjacent pairs of baffles 86 and 88. Accordingly in this preferred embodiment, cooling passageway 82 is substantially displaced out of reaction chambers 18a and 20a. Accordingly, cooling is provided between a pair of immediately adjacent baffles. Such provides but one alternate example of providing desired cooling within a reactor vessel. Such also provides some advantages over the first described embodiment. Specifically, more ultraviolet light tubes can be placed within each respective reaction chamber as the cooling function is displaced from such chambers. Further, such provides a cooling function inherently to the liner. This provides a desired colder surface for collecting any reactant condensation product, and also maintains a higher level of moisture within the cementitious liner which increases the percentage of the reagent present in the liner which is utilized.

Figure 8:
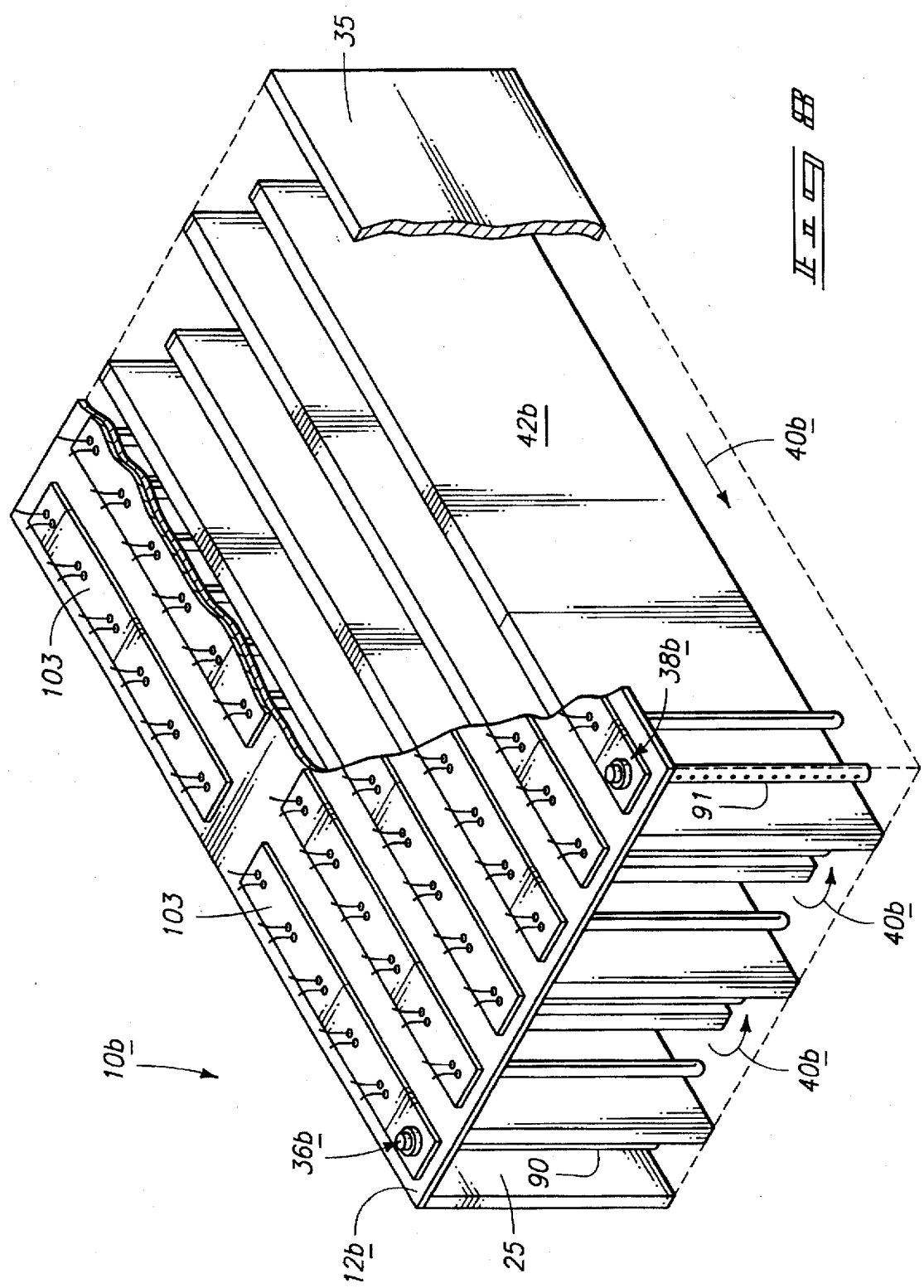
FIG. 8 is a diagrammatic perspective view of an alternate preferred embodiment apparatus for photochemically oxidizing gaseous volatile or semi-volatile organic compounds in accordance with the invention.
Figure 9:
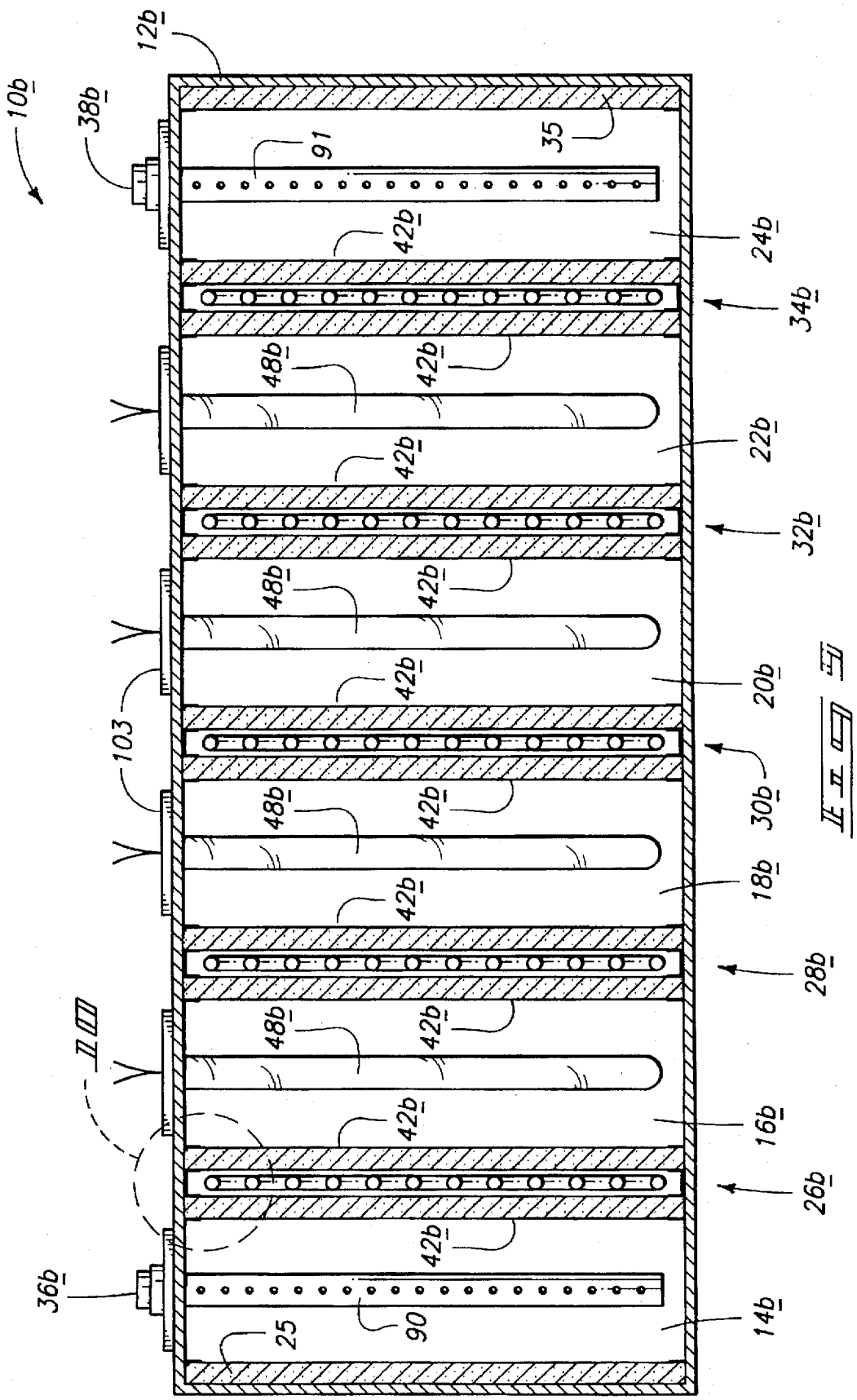
FIG. 9 is an enlarged diagrammatic end view of the FIG. 8 apparatus.

An alternate preferred embodiment is shown and described with reference to FIGS. 8–14. Like numerals from the first described embodiment are utilized where appropriate, with differences being indicated with the suffix "b" or with different numerals. Referring to FIGS. 8 and 9, sidewall/baffle apparatus 25, 26b, 28b, 30b, 32b, 34b, and 35 are constructed such that individual baffles are removable from an end of reactor vessel 12b. Further, gas flow path 40b is oriented to run generally along the length of the reactor vessel in multiple passes, as opposed to laterally up and down as in the first described embodiment.

Also, the ultraviolet light source is provided in the form of U-shaped ultraviolet light tubes which extend into the respective reaction chambers. Light tubes 48b extend downwardly into the chamber from a series of plates 103. This enables a plurality of a set of individual light tubes to be removed as might be necessary for changing spent light tubes or for cleaning the light tubes. Gas inlet 36b and gas outlet 38b include respective corrosion resistant (for example, Teflon®-coated) tubes 90 and 91 which extend downwardly into the gas flow path. Each includes a plurality of holes as shown to serve as a gas diffusion and collection source (see also FIG. 14).

Reference is next made to FIGS. 11 and 12 for description of an alternate baffle and frame design 102. Such comprises an aluminum frame member 104 extending essentially peripherally around the baffle. Dry porous cementitious and chemically sorbent material 105, such as described above, is received within peripheral frame 104. Frame member 104 comprises a peripheral and inwardly facing channel member having at least two channel walls 106 and 108. Such comprise at least one projection extending into the dry porous cementitious and chemically sorbent material 105. In the illustrated and preferred embodiment, a projection 110 extends generally perpendicularly from channel wall 106 into the cementitious material, with a projection 112 extending generally perpendicular into the cementitious material from channel wall 108. Accordingly, such projections generally face towards one another.

Frame 104 can be considered as a structural support member. Projections 110 and 112 constitute portions of frame 104 which are surrounded by the dry porous cementitious and chemically sorbent material 105. Peripheral frame 104 principally provides a protection for the edges of the baffle such that the baffles can be slid easily into and out of the reactor vessel without crumbling or otherwise damaging such edges. Frame 104 also provides a suitable mold for defining the shape of the baffles. The baffles are, however, otherwise substantially self-supporting such that the peripheral frame can be separated from the cementitious material after hardening. Projections 110 and 112 could be eliminated to facilitate removal of peripheral frame 104 from the hardened cementitious material is such were desired. The FIGS. 8–14 embodiment differs in part from the first described embodiment in that cross-support members are not utilized as in the first described embodiment.

An alternate formulation has also been developed for the cementitious material of the baffle design. A preferred process for assembling baffle apparatus 102 would be to initially place framework 104 upon a suitable surface such as wood, or on paper supported on a hard surface. A dry mixture of material is combined with water to form a slurry which is received within the framework such that the slurry completely fills the volume and area internal of peripheral frame 104. An example dry mixture by weight for such purpose comprises from about 23% to 35% cement; from about 30% to 45% added CaO; from about 6% to 20% added $Ca(OH)_2$; and from about 10% to 25% added $CaSO_4$. A more preferred range for the added $CaSO_4$ is from about 16% to 18% by weight of added material. One exemplary preferred composition for the dry mixture by weight is 29.9% Type III Portland Cement; 33.0% CaO; 13.9% $Ca(OH)_2$; 16.6% $CaSO_4$; and 6.6% fiberglass. Addition of the $CaSO_4$ in this described embodiment facilitates reduction or elimination of carbon dioxide treated $Ca(OH)_2$ and added $Al_2O_3$ while still achieving reasonable initial set times for the cement.

The cement preferably comprises or consists essentially of Portland Cement, such as Type III Portland Cement. Alternately, a high content alumina-based cement such as the Fondue cement described above could of course be utilized.

The slurry is also preferably provided to have from about 0.5% to 10% fiberglass by weight of the dry mixture, which can of course be provided initially with the dry mixture or added to the slurry after initial formation.

The slurry is preferably separately formed and mixed in a vessel, and then poured into the frame to form a desired reactor sidewall shape. The dry mixture and fiberglass preferably constitute about 55% by weight of the slurry composition, with the remaining 45% constituting water. Such is allowed to thereafter harden within the frame into a hard, cement reactor sidewall.

Figure 10:
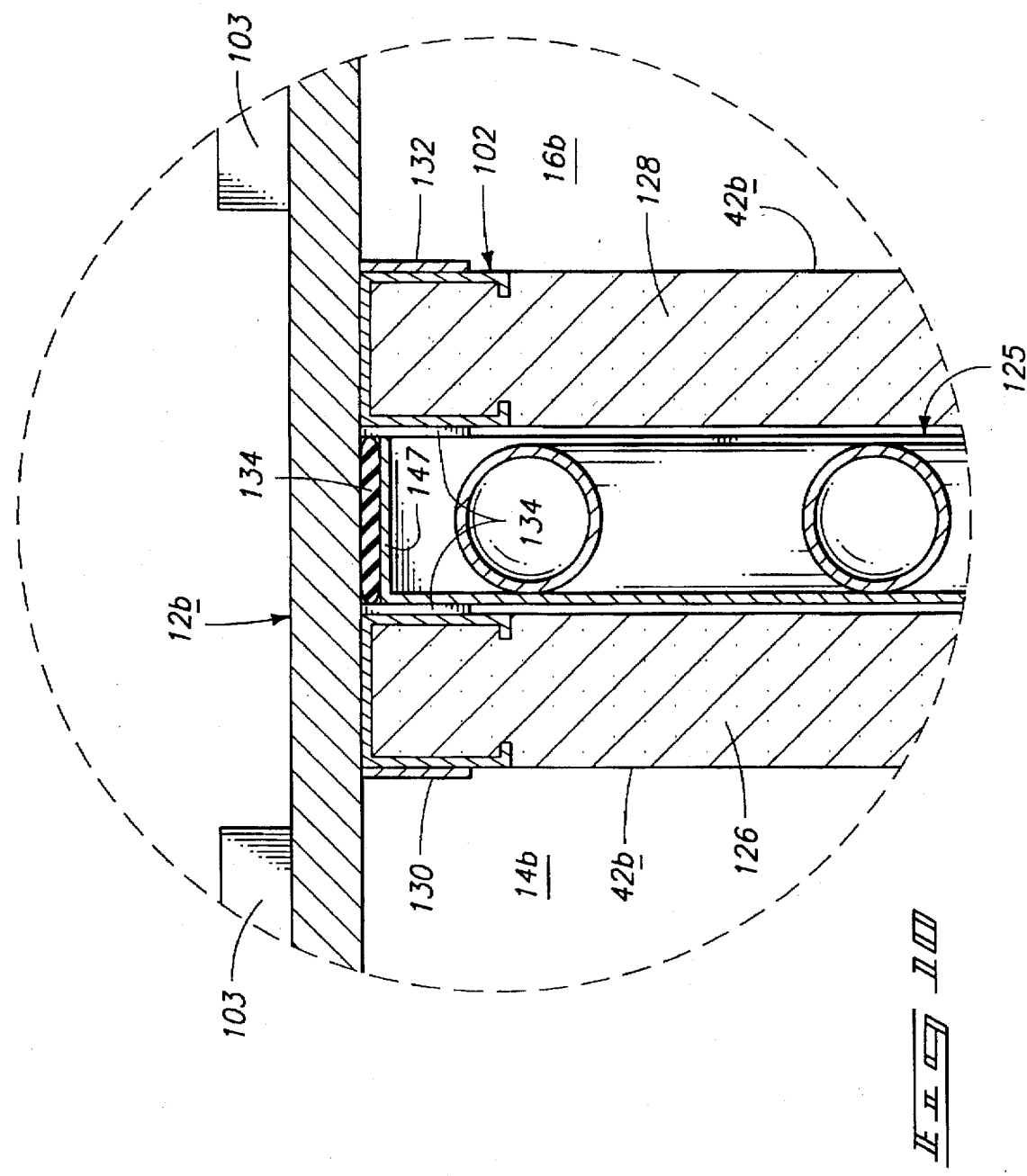
FIG. 10 is an enlarged view of a portion of FIG. 9

Reference is now made to FIGS. 9 and 10 where an alternate cooling and mounting assembly for individual baffles are provided. Such illustrates a cooling medium 125 positioned adjacent and sandwiched between a pair of the above-described FIGS. 11 and 12 baffle assemblies, which are also indicated in the enlarged view with numerals 126 and 128. Baffles 126, 128 and cooling medium 125 are slidably retained relative to the reactor vessel at the top and bottom of said vessel by respective pairs of channels 130 and 132 which project into the vessel. A series of pins 134 projects into the reactor vessel substantially parallel with channel members 130 and 132 and position baffle assemblies 126 and 128 peripherally of cooling medium 125. Cooling medium 125 is essentially sandwiched between and retained upright by pins 134. A suitable sealing gasket 134 is provided at the top and bottom of cooling medium assembly 125, essentially providing a fluid tight seal between chambers 14b and 16b where the baffle and cooling medium assembly joins with the reactor floor and ceiling.

Referring to FIG. 13, a preferred cooling medium 125 is comprised of continuous corrosion resistant (i.e., Teflon®-coated copper) tubing 140 arranged in a coil-like manner relative to a suitable substrate 145. A cooling fluid (i.e., air or water) flows through tubing 140 during operation. Substrate 145 comprises a metal sheet to which tubing 140 is retained by suitable retainers 146. Metal substrate or sheet 145 includes peripheral raised edges 147, although the overall substrate is preferably substantially planar as shown.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

We claim:

1. An apparatus for photochemically oxidizing gaseous volatile or semi-volatile organic compounds comprising:

a reactor vessel having a plurality of reaction chambers provided therein, the reaction chambers having respective chamber lining sidewalls;

a source of ultraviolet light provided within the reaction chambers to oxidize gaseous volatile or semi-volatile organic compounds fed to the reaction chambers into gaseous oxidation products;

the sidewalls of the reaction chambers comprising a dry porous cementitious and chemically sorbent material, the sorbent material being chemically reactive with the gaseous oxidation products to produce solid reaction products incorporated in the reaction chamber sidewalls;

the sidewalls of the reaction chambers comprising at least one baffle mounted relative to the reactor vessel, the baffle defining a gas flow path within the reactor vessel between a gas inlet and a gas outlet, the baffle comprising at least a portion of the respective reaction chamber sidewalls with the baffle itself comprising the dry porous cementitious and chemically sorbent material; and a cooling medium adjacent the baffle to cool the baffles, the cooling medium comprising tubing.

2. The apparatus for photochemically oxidizing gaseous volatile or semi-volatile organic compounds of claim 1 further comprising a substrate to which the tubing is attached.

3. The apparatus for photochemically oxidizing gaseous volatile or semi-volatile organic compounds of claim 1 further comprising a substantially planar substrate to which the tubing is attached.

4. The apparatus for photochemically oxidizing gaseous volatile or semi-volatile organic compounds of claim 1 further comprising a substrate to which the tubing is attached, the substrate being mounted for sliding removable receipt relative to the reactor vessel.

5. An apparatus for photochemically oxidizing gaseous volatile or semi-volatile organic compounds comprising:

a reactor vessel having a plurality of reaction chambers provided therein, the reaction chambers having respective chamber lining sidewalls;

a source of ultraviolet light provided within the reaction chambers to oxidize gaseous volatile or semi-volatile organic compounds fed to the reaction chambers into gaseous oxidation products, the source of ultraviolet light comprising at least one U-shaped ultraviolet light tube extending into the respective reaction chambers;

the sidewalls of the reaction chambers comprising a dry porous cementitious and chemically sorbent material, the sorbent material being chemically reactive with the gaseous oxidation products to produce solid reaction products incorporated in the reaction chamber sidewalls; and the sidewalls of the reaction chambers comprising at least one baffle mounted relative to the reactor vessel, the baffle defining a gas flow path within the reactor vessel between a gas inlet and a gas outlet, the baffle comprising at least a portion of the respective reaction chamber sidewalls with the baffle itself comprising the dry porous cementitious and chemically sorbent material.

6. The apparatus for photochemically oxidizing gaseous volatile or semi-volatile organic compounds of claim 5 comprising multiple U-shaped ultraviolet light tubes per chamber.

7. An apparatus for photochemically oxidizing gaseous volatile or semi-volatile organic compounds comprising:

a reactor vessel having a plurality of reaction chambers provided therein, the reaction chambers having respective chamber lining sidewalls;

a source of ultraviolet light provided within the reaction chambers to oxidize gaseous volatile or semi-volatile organic compounds fed to the reaction chambers into gaseous oxidation products;

the sidewalls of the reaction chambers comprising a dry porous cementitious and chemically sorbent material, the sorbent material being chemically reactive with the gaseous oxidation products to produce solid reaction products incorporated in the reaction chamber sidewalls;

the sidewalls of the reaction chambers comprising at least two baffles mounted relative to the reactor vessel, the baffles defining a gas flow path within the reactor vessel between a gas inlet and a gas outlet, the baffles comprising at least a portion of the respective reaction chamber sidewalls with the baffles themselves comprising the dry porous cementitious and chemical sorbent material; and further comprising at least one cooling fluid passageway received within the reactor vessel, the cooling fluid passageway being sandwiched between the at least two baffles, the cooling fluid passageway comprising tubing.

8. The apparatus for photochemically oxidizing gaseous volatile or semi-volatile organic compounds of claim 7 further comprising a substrate to which the tubing is attached.

9. The apparatus for photochemically oxidizing gaseous volatile or semi-volatile organic compounds of claim 7 further comprising a substantially planar substrate to which the tubing is attached.

10. The apparatus for photochemically oxidizing gaseous volatile or semi-volatile organic compounds of claim 7 further comprising a substrate to which the tubing is attached, the substrate being mounted for sliding removable receipt relative to the reactor vessel.

11. An apparatus for photochemically oxidizing gaseous volatile or semi-volatile organic compounds comprising:

a reactor vessel having a plurality of reaction chambers provided therein, the reaction chambers having respective chamber lining sidewalls;

a source of ultraviolet light provided within the reaction chambers to oxidize gaseous volatile or semi-volatile organic compounds fed to the reaction chambers into gaseous oxidation products;

the sidewalls of the reaction chambers comprising a dry porous cementitious and chemically sorbent material, the sorbent material being chemically reactive with the gaseous oxidation products to produce solid reaction products incorporated in the reaction chamber sidewalls; and the sidewalls of the reaction chambers comprising at least one baffle mounted relative to the reactor vessel, the baffle defining a gas flow path within the reactor vessel between a gas inlet and a gas outlet, the baffle comprising at least a portion of the respective reaction chamber sidewalls with the baffle itself comprising the dry porous cementitious and chemically sorbent material, the baffle comprising a peripheral frame, the dry porous cementitious and chemically sorbent material being received within the peripheral frame, the frame comprising a peripheral and inwardly facing channel member having at least two channel walls, the channel walls comprising at least one projection extending into the dry porous cementitious and chemically sorbent material.

12. The apparatus for photochemically oxidizing gaseous volatile or semi-volatile organic compounds of claim 11 comprising at least two projections extending into the dry porous cementitious and chemically sorbent material from the channel walls.

13. The apparatus for photochemically oxidizing gaseous volatile or semi-volatile organic compounds of claim 11 comprising at least two projections extending into the dry porous cementitious and chemically sorbent material from the channel walls, said two projections facing generally towards one another.

14. The apparatus for photochemically oxidizing gaseous volatile or semi-volatile organic compounds of claim 11 comprising at least one projection extending into the dry porous cementitious and chemically sorbent material from each of the two channel walls.

15. The apparatus for photochemically oxidizing gaseous volatile or semi-volatile organic compounds of claim 11 wherein the projection extends generally perpendicular from one of the channel walls.

16. The removable reaction chamber baffle liner of claim 11 wherein the hardened mass of dry porous cementitious and chemically sorbent material comprises interspersed structural reinforcing fiberglass.

17. A removable reaction chamber baffle liner for a photochemical oxidation reactor vessel for oxidizing volatile or semi-volatile organic compounds, the baffle liner comprising:

a peripheral frame sized and shaped for sliding receipt within the photochemical oxidation reactor vessel, the reactor vessel having a plurality of reaction chambers provided therein which are defined by at least one baffle liner, the reaction chambers having respective chamber lining sidewalls defined by the baffle liner, the baffle liner defining a gas flow path within the reactor vessel between a gas inlet and a gas outlet, the reactor vessel comprising a source of ultraviolet light provided within the reaction chambers to oxidize gaseous volatile or semi-volatile organic compounds fed to the reaction chambers into gaseous oxidation products; and a hardened mass of dry porous cementitious and chemically sorbent material received within the peripheral frame, the sorbent material being chemically reactive with the gaseous oxidation products to produce solid reaction products incorporated in the material.

18. The removable reaction chamber baffle liner of claim 17 wherein the peripheral frame comprises a peripheral and inwardly facing channel member.

19. The removable reaction chamber baffle liner of claim 17 wherein the hardened mass of dry porous cementitious and chemically sorbent material comprises interspersed structural reinforcing fiberglass.

20. A removable reaction chamber baffle liner for a photochemical oxidation reactor vessel for oxidizing volatile or semi-volatile organic compounds, the baffle liner comprising:

a peripheral frame sized and shaped for sliding receipt within the photochemical oxidation reactor vessel, the reactor vessel having a plurality of reaction chambers provided therein which are defined by at least one baffle liner, the reaction chambers having respective chamber lining sidewalls defined by the baffle liner, the baffle liner defining a gas flow path within the reactor vessel between a gas inlet and a gas outlet, the reactor vessel comprising a source of ultraviolet light provided within the reaction chambers to oxidize gaseous volatile or semi-volatile organic compounds fed to the reaction chambers into gaseous oxidation products;

a hardened mass of dry porous cementitious and chemically sorbent material received within the peripheral frame, the sorbent material being chemically reactive with the gaseous oxidation products to produce solid reaction products incorporated in the material; and the peripheral frame comprising a peripheral and inwardly facing channel member having at least two channel walls, the channel walls comprising at least one projection extending into the dry porous cementitious and chemically sorbent material.

21. The removable reaction chamber baffle liner of claim 20 comprising at least two projections extending into the dry porous cementitious and chemically sorbent material from the channel walls.

22. The removable reaction chamber baffle liner of claim 20 comprising at least two projections extending into the dry porous cementitious and chemically sorbent material from the channel walls, said two projections facing generally towards one another.

23. The removable reaction chamber baffle liner of claim 20 comprising at least one projection extending into the dry porous cementitious and chemically sorbent material from each of the two channel walls.

24. The removable reaction chamber baffle liner of claim 20 wherein the projection extends generally perpendicular from one of the channel walls.

25. The removable reaction chamber baffle liner of claim 20 wherein the hardened mass of dry porous cementitious and chemically sorbent material comprises interspersed structural reinforcing fiberglass.

26. A removable reaction chamber baffle liner comprising:

at least one structural support member;

a hardened mass of dry porous cementitious and chemically sorbent material surrounding at least a portion of the structural support member, the hardened mass of dry porous cementitious and chemically sorbent material with support member being sized and shaped for removable receipt within a photochemical oxidation reactor vessel for oxidizing volatile or semi-volatile organic compounds, the reactor vessel having a plurality of reaction chambers provided therein which are defined by at least one of said baffle liner, the reaction chambers having respective chamber lining sidewalls defined by the baffle liner, the baffle liner defining a gas flow path within the reactor vessel between a gas inlet and a gas outlet, the reactor vessel comprising a source of ultraviolet light provided within the reaction chambers to oxidize gaseous volatile or semi-volatile organic compounds fed to the reaction chambers into gaseous oxidation products, the sorbent material of the baffle liner being chemically reactive with the gaseous oxidation products to produce solid reaction products incorporated in the material; and wherein the structural support member comprises a frame member, the frame member comprising an inwardly facing channel member having at least two channel walls, the channel walls comprising at least one projection extending into the dry porous cementitious and chemically sorbent material, the projection comprising said portion of the structural support member surrounded by the dry porous cementitious and chemically sorbent material.

27. The removable reaction chamber baffle liner of claim 26 wherein the hardened mass of dry porous cementitious and chemically sorbent material comprises interspersed structural reinforcing fiberglass.

28. The removable reaction chamber baffle liner of claim 26 comprising at least one projection extending into the dry porous cementitious and chemically sorbent material from each of the two channel walls.

29. The removable reaction chamber baffle liner of claim 26 wherein the projection extends generally perpendicular from one of the channel walls.

* * * * *